United States Patent
Mann et al.

(10) Patent No.: US 8,609,588 B2
(45) Date of Patent: Dec. 17, 2013

(54) SYNERGISTIC HERBICIDAL COMPOSITION CONTAINING PENOXSULAM AND GLYPHOSATE

(75) Inventors: Richard K. Mann, Franklin, IN (US); Ändrea Christine McVeigh-Nelson, Indianapolis, IN (US)

(73) Assignee: Dow AgroSciecnes, LLC., Indianapolis, IN (US)

( * ) Notice: Subject to any disclaimer, the term of this patent is extended or adjusted under 35 U.S.C. 154(b) by 0 days.

(21) Appl. No.: 13/365,323

(22) Filed: Feb. 3, 2012

(65) Prior Publication Data

US 2012/0202693 A1    Aug. 9, 2012

Related U.S. Application Data

(60) Provisional application No. 61/439,478, filed on Feb. 4, 2011.

(51) Int. Cl.
*A01N 57/08* (2006.01)
*A01N 57/18* (2006.01)
*A01N 43/60* (2006.01)
*A01N 43/90* (2006.01)

(52) U.S. Cl.
USPC ............ 504/128; 504/136; 504/206; 504/241

(58) Field of Classification Search
USPC .......................... 504/128, 118, 206, 241, 136
See application file for complete search history.

(56) References Cited

U.S. PATENT DOCUMENTS

| 5,858,924 A | 1/1999 | Johnson et al. | |
|---|---|---|---|
| 2006/0183637 A1* | 8/2006 | Loughner et al. | ............. 504/101 |
| 2009/0042728 A1 | 2/2009 | Loughner et al. | |
| 2010/0279862 A1 | 11/2010 | Bickers et al. | |

OTHER PUBLICATIONS

Roundup Pro Herbicide. Label [online]. AFPMB, 2002 [retrieved on Dec. 3, 2012]. Retrieved from the Internet:<http://www.afpmb.org/sites/default/files/pubs/standardlists/labels/6840-01-108-9578_label_roundup_pro.pdf> 9 pages.*

Disclosed Anonymously 462055: "2-(2,2-difluoroethoxy)-6-trifluoromethy1-N-(5,8-dimethoxy[1,2,4]triazolo[1,5-c] pyrimidin-2-y1)benzenesfulfonamide and its use as a herbicide in mixtures" Research Disclosure, Oct. 2002, pp. 1832-1833.

"Penoxsulam and Its Use as a Herbicide in Mixtures for Use in Rice, Wheat, Barely, Oats, Sorghum, Corn, Maize, Ivm, Rangeland Pastures, Grasslands, Fallowland, Turf, and Aquatics" The IP.com Journal, vol. 5, No. 4, Apr. 2005, pp. 286-293.

* cited by examiner

*Primary Examiner* — John Pak
*Assistant Examiner* — Andriae M Holt
(74) *Attorney, Agent, or Firm* — Robert Chang

(57) ABSTRACT

A synergistic mixture of penoxsulam and glyphosate controls weeds in crops, especially vines, range and pasture, industrial vegetation management, rights of way and in any glyphosate tolerant crop.

6 Claims, No Drawings

SYNERGISTIC HERBICIDAL COMPOSITION CONTAINING PENOXSULAM AND GLYPHOSATE

CROSS REFERENCE TO RELATED APPLICATIONS

This application claims the benefit of U.S. Provisional Patent Application Ser. No. 61/439,478 filed Feb. 4, 2011.

FIELD OF THE INVENTION

This invention concerns a synergistic herbicidal composition containing (a) penoxsulam and (b) glyphosate for controlling the growth of undesirable vegetation, especially in vines, range and pasture, industrial vegetation management, rights of way and in any glyphosate tolerant crop. These compositions are disclosed as providing improved post-emergence herbicidal weed control.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Ninth Edition, 2007, p. 429 "'synergism' [is] an interaction of two or more factors such that the effect when combined is greater than the predicted effect based on the response to each factor applied separately." The present invention is based on the discovery that penoxsulam and glyphosate, already known individually for their herbicidal efficacy, display a synergistic effect when applied in combination.

SUMMARY OF THE INVENTION

The present invention concerns a synergistic herbicidal mixture comprising an herbicidally effective amount of (a) penoxsulam and (b) glyphosate. The compositions may also contain an agriculturally acceptable adjuvant and/or carrier.

The present invention also concerns herbicidal compositions for and methods of controlling the growth of undesirable vegetation, particularly in range and pasture, industrial vegetation management, rights of way and in any glyphosate tolerant crop, and the use of these synergistic compositions.

The species spectra of penoxsulam and glyphosate, i.e., the weed species which the respective compounds control, are broad and highly complementary. It has now been found that a combination of penoxsulam and glyphosate exhibits a synergistic action in the control broadleaf signalgrass (*Brachiaria platyphylla*, BRAPP), yellow nutsedge (*Cyperus esculentus*, CYPES), barnyardgrass (*Echinochloa crus-galli*, ECHCG), morningglory (*Ipomoea, hederacea*, IPOHE), Chinese sprangletop (*Leptochloa chinensis*, LEFCH), ryegrass (*Lolium* spp, LOLSS), scented mayweed (*Matricaria chamomilla*, MATCH), and annual bluegrass (*Poa annua*, POAAN) at application rates equal to or lower than the rates of the individual compounds.

DETAILED DESCRIPTION OF THE INVENTION

Penoxsulam is the common name for 2-(2,2-difluoroethoxy)-N-(5,8-dimethoxy-[1,2,4]triazolo[1,5-c]pyrimidin-2-yl)-6-(trifluoromethyl)benzenesulfonamide. Its herbicidal activity is described in The Pesticide Manual, Fifteenth Edition, 2009. Penoxsulam controls *Echinochloa* spp., as well as many broadleaf, sedge and aquatic weeds in rice, and *Apera* spp. grass in cereals, as well as many broadleaf weeds in aquatics, many cereal crops, range and pasture, IVM and turf.

Glyphosate, N-(phosphonomethyl)glycine is a EPSP synthase inhibitor. Its herbicidal activity is described in *The Pesticide Manual*, Fifteenth Edition, 2009. Glyphosate provides non-selective post-emergence weed control.

The term herbicide is used herein to mean an active ingredient that kills, controls or otherwise adversely modifies the growth of plants. An herbicidally effective or vegetation-controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of glyphosate to penoxsulam at which the herbicidal effect is synergistic lies within the range from about 3:2 to about 896:1, preferably from about 4:1 to about 448:1. The rate at which the synergistic composition is applied will depend upon the particular type of weed to be controlled, the degree of control required, and the timing and method of application. In general, the composition of the invention can be applied at an application rate from about 112.5 grams of active ingredient per hectare (gai/ha) to about 2310 gai/ha based on the total amount of active ingredients in the composition. Penoxsulam is applied at a rate from about 2.5 g/ha to about 70 g/ha and glyphosate is applied at a rate from about 110 g/ha to about 2240 g/ha.

The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank-mixed with the other herbicide or herbicides or applied sequentially with the other herbicide or herbicides. Some of the herbicides that can be employed in conjunction with the synergistic composition of the present invention include: 4-CPA; 4-CPB;

4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlomitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, pentachlorophenol, pentanochlor, pentoxazone, perfluidone, pethoxamid, phenisopham, phenmedipham, phenmediphamethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac tritosulfuron, vernolate, xylachlor and salts, esters, optically active isomers and mixtures thereof.

The synergistic composition of the present invention can, further, be used in conjunction with glufosinate, dicamba, imidazolinones, sulfonylureas, or 2,4-D on glyphosate-tolerant, glufosinate-tolerant, dicamba-tolerant, imidazolinone-tolerant, sulfonylurea-tolerant and 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, harpin proteins, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water-dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono- and dialkyl phosphate esters; vegetable or seed oils such as soybean oil, rapeseed/canola oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils, particularly methyl esters.

Oftentimes, some of these materials, such as vegetable or seed oils and their esters, can be used interchangeably as an agricultural adjuvant, as a liquid carrier or as a surface active agent.

Other additives commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.1 to 98 percent by weight. Concentrations from 10 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before making a postemergence, foliar application to exposed weed and crop foliage, or applied as a dry or liquid formulation directly into flooded rice fields. The diluted compositions usually applied as a postemergence, foliar application to weeds or the locus of weeds generally contain 0.25 to 20 weight percent active ingredient and preferably contain 0.4 to 14 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

EXAMPLES

Evaluation of Postemergence Herbicidal Activity of Mixtures in the Greenhouse

Seeds of the desired test plant species were planted in 80% mineral soil/20% grit planting mixture, which typically has a pH of 7.2 and an organic matter content of about 2.9 percent, in plastic pots with a surface area of 128 square centimeters ($cm^2$). The growing medium was steam sterilized. The plants were grown for 7-19 days in a greenhouse with an approximate 14-hour (h) photoperiod which was maintained at about 29° C. during the day and 26° C. during the night. Nutrients and water were added on a regular basis and supplemental lighting was provided with overhead metal halide 1000-Watt lamps as necessary. The plants were treated with postemergence foliar applications when they reached the second to fourth true leaf stage. All treatments were applied using a randomized complete block trial design, with 4 replications per treatment.

Formulated amounts of penoxsulam and glyphosate IPA salt were placed in 60 milliliter (mL) glass vials and dissolved in a volume of 60 mL of a water solution containing Agri-dex crop oil concentrate in a 1% volume per volume (v/v) ratio.

Compound requirements are based upon a 12 mL application volume at a rate of 187 liters per hectare (L/ha). Spray solutions of the mixtures were prepared by adding the stock solutions to the appropriate amount of dilution solution to form 12 mL spray solution with active ingredients in single and two way combinations. Formulated compounds were applied to the plant material with an overhead Mandel track sprayer equipped with 8002E nozzles calibrated to deliver 187 L/ha at a spray height of 18 inches (43 centimeters (cm)) above average plant canopy. The weed spectrum included broadleaf signalgrass (*Brachiaria platyphylla*, BRAPP), yellow nutsedge (*Cyperus esculentus*, CYPES), barnyardgrass (*Echinochloa crus-galli*, ECHCG), morningglory (*Ipomoea, hederacea*, IPOHE), and Chinese sprangletop (*Leptochloa chinensis*, LEFCH).

The treated plants and control plants were placed in a greenhouse as described above and watered by sub-irrigation to prevent wash-off of the test compounds. Treatments were rated at 16 days after application (DAA) as compared to the untreated control plants. Visual weed control was scored on a scale of 0 to 100 percent where 0 corresponds to no injury and 100 corresponds to complete kill. Results are reported in Tables 1-3.

Evaluation of Postemergence Herbicidal Activity of Mixtures under Field Conditions Methodology Trial site was located in commercially grown vines of European grape (*Vitis vinifera*). The trial was conducted using normal research methodology. Trial plots were between 2 m wide by 6 10 m long. All treatments were applied using a randomized complete block trial design with 3 replications per treatment. The trial sites had naturally occurring populations of weeds. The weed spectrum included, but was not limited to, ryegrass (*Lolium* spp, LOLSS), scented mayweed (*Matricaria chamomilla*, MATCH), and annual bluegrass (*Poa annua*, POAAN).

Treatments consisted of tank mixes of an oil dispersion of penoxsulam and commercially available formulation of glyphosate applied in water. The application volume was 250 liters per hectare (L/ha). Application was made using a precision gas hand sprayer at 250 kPA pressure using a 2 m boom with flat fan (80015VS) nozzles to broadcast the treatments to the weeds and to the soil.

The treated and control pots were rated blind at various intervals after application, with the last evaluation taken 16 days after application. Ratings were based on Percent (%) Visual weed control, where 0 corresponds to no control and 100 corresponds to complete control. Results are reported in Table 4.

Evaluation

Data was collected and analyzed using various statistical methods.

Colby's equation was used to determine the herbicidal effects expected from the mixtures (Colby, S. R. Calculation of the synergistic and antagonistic response of herbicide combinations. *Weeds* 1967 15, 20-22).

The following equation was used to calculate the expected activity of mixtures containing two active ingredients, A and B:

$$\text{Expected} = A + B - (A \times B / 100)$$

A=observed efficacy of active ingredient A at the same concentration as used in the mixture;

B=observed efficacy of active ingredient B at the same concentration as used in the mixture.

The results are summarized in Tables 1-4.

TABLE 1

Control of CYPES and LEFCH in the greenhouse with Penoxsulam plus 53 grams ai/ha of Glyphosate

| Penoxsulam | Glyphosate | Days After | CYPES | | LEFCH | |
|---|---|---|---|---|---|---|
| (rate in grams ai/ha) | | Application | Obs | Exp* | Obs | Exp* |
| 1.3 | 0 | 16 | 5.8 | — | — | — |
| 0 | 53 | 16 | 8.2 | — | — | — |
| 1.3 | 53 | 16 | 47 | 13.6 | — | — |
| 2.5 | 0 | 16 | 31.8 | — | — | — |
| 0 | 53 | 16 | 8.2 | — | — | — |
| 2.5 | 53 | 16 | 73.5 | 37.1 | — | — |
| 5 | 0 | 16 | — | — | — | — |
| 0 | 53 | 16 | — | — | — | — |
| 5 | 53 | 16 | — | — | — | — |
| 10 | 0 | 16 | — | — | 6.3 | — |
| 0 | 53 | 16 | — | — | 1 | — |
| 10 | 53 | 16 | — | — | 22.5 | 7.4 |

CYPES = yellow nutsedge, *Cyperus esculentus*
LEFCH = Chinese sprangletop, *Leptochloa chinensis*
grams ai/ha = grams of active ingredient per hectare
Obs = Observed control (%)
Exp* = Expected control (%)

TABLE 2

Control of CYPES and BRAPP in the greenhouse with Penoxsulam plus 110 grams ai/ha of Glyphosate

| Penoxsulam | Glyphosate | Days After | CYPES | | BRAPP | |
|---|---|---|---|---|---|---|
| (rate in grams ai/ha) | | Application | Obs | Exp* | Obs | Exp* |
| 1.3 | 0 | 16 | 6 | — | 9 | — |
| 0 | 110 | 16 | 17 | — | 15 | — |
| 1.3 | 110 | 16 | 60 | 22 | 47 | 23 |
| 2.5 | 0 | 16 | — | — | 10 | — |
| 0 | 110 | 16 | — | — | 15 | — |
| 2.5 | 110 | 16 | — | — | 45 | 23 |
| 5 | 0 | 16 | 44 | — | 4 | — |
| 0 | 110 | 16 | 17 | — | 15 | — |
| 5 | 110 | 16 | 83 | 52 | 39 | 18 |
| 10 | 0 | 16 | 65 | — | — | — |
| 0 | 110 | 16 | 17 | — | — | — |
| 10 | 110 | 16 | 86 | 71 | — | — |

CYPES = yellow nutsedge, *Cyperus esculentus*
BRAPP = broadleaf signalgrass, *Brachiaria platyphylla*
grams ai/ha = grams of active ingredient per hectare
Obs = Observed control (%)
Exp* = Expected control (%)

TABLE 3

Control of CYPES, ECHCG, IPOHE and LEFCH in the greenhouse with Penoxsulam plus 210 grams ai/ha of Glyphosate

| Penoxsulam | Glyphosate | Days After | CYPES | | ECHCG | | IPOHE | | LEFCH | |
|---|---|---|---|---|---|---|---|---|---|---|
| (rate in grams ai/ha) | | Application | Obs | Exp* | Obs | Exp* | Obs | Exp* | Obs | Exp* |
| 1.3 | 0 | 16 | 6 | — | 63 | — | 16 | — | 5 | — |
| 0 | 210 | 16 | 25 | — | 17 | — | 31 | — | 41 | — |

TABLE 3-continued

Control of CYPES, ECHCG, IPOHE and LEFCH in the greenhouse with Penoxsulam plus 210 grams ai/ha of Glyphosate

| Penoxsulam | Glyphosate | Days After | CYPES | | ECHCG | | IPOHE | | LEFCH | |
|---|---|---|---|---|---|---|---|---|---|---|
| (rate in grams ai/ha) | | Application | Obs | Exp* | Obs | Exp* | Obs | Exp* | Obs | Exp* |
| 1.3 | 210 | 16 | 66 | 29 | 78 | 70 | 61 | 42 | 69 | 45 |
| 2.5 | 0 | 16 | 32 | — | 62 | — | 31 | — | 1 | — |
| 0 | 210 | 16 | 25 | — | 17 | — | 31 | — | 41 | — |
| 2.5 | 210 | 16 | 80 | 49 | 84 | 69 | 67 | 59 | 82 | 42 |
| 5 | 0 | 16 | 44 | — | — | — | 31 | — | 2 | — |
| 0 | 210 | 16 | 25 | — | — | — | 31 | — | 41 | — |
| 5 | 210 | 16 | 87 | 58 | — | — | 65 | 53 | 85 | 42 |
| 10 | 0 | 16 | 65 | | — | — | 31 | — | 6 | |
| 0 | 210 | 16 | 25 | — | — | — | 31 | — | 41 | |
| 10 | 210 | 16 | 89 | 74 | — | — | 71 | 53 | 86 | 45 |

CYPES = yellow nutsedge, *Cyperus esculentus*
LEFCH = Chinese sprangletop, *Leptochloa chinensis*
ECHCG = barnyardgrass, *Echinochloa crus-galli*
IPOHE = morningglory, *Ipomoea hederacea*
grams ai/ha = grams of active ingredient per hectare
Obs = Observed control (%)
Exp* = Expected control (%)

TABLE 4

Synergistic control of MATCH, POAAN and LOLSS in the field with 20 + 720 grams ai/ha of Penoxsulam + Glyphosate, respectively

| Penoxsulam | Glyphosate | Days After | MATCH | | POAAN | | LOLSS | |
|---|---|---|---|---|---|---|---|---|
| (rate in grams ai/ha) | | Application | Obs | Exp* | Obs | Exp* | Obs | Exp* |
| 20 | 0 | 27 | 0 | — | 0 | — | — | — |
| 0 | 720 | 27 | 50 | — | 93 | — | — | — |
| 20 | 720 | 27 | 100 | 50 | 100 | 93 | — | — |
| 20 | 0 | 61 | — | — | — | — | 0 | — |
| 0 | 720 | 61 | — | — | — | — | 60 | — |
| 20 | 720 | 61 | — | — | — | — | 93 | 60 |

LOLSS = ryegrass, *Lolium* spp.
MATCH = scented mayweed, *Matricaria chamomilla*
POAAN = annual bluegrass, *Poa annua*
grams ai/ha = grams of active ingredient per hectare
Obs = Observed control (%)
Exp* = Expected control (%)

What is claimed is:

1. A synergistic herbicidal mixture comprising an herbicidally effective amount of (a) penoxsulam and (b) glyphosate, wherein the weight ratio of glyphosate to penoxsulam is from 5.3:1 to 210:1.3.

2. The synergistic herbicidal mixture of claim 1 in which glyphosate is an agriculturally acceptable salt.

3. An herbicidal composition comprising an herbicidally effective amount of the synergistic herbicidal mixture of claim 1 and an agriculturally acceptable adjuvant and/or carrier.

4. A method of controlling undesirable vegetation which comprises contacting the vegetation or the locus thereof with an herbicidally effective amount of the synergistic herbicidal mixture of claim 1.

5. The method of claim 4 wherein the undesirable vegetation is in vines, pasture, rangeland, industrial vegetation management, aquatics or turf.

6. The method of claim 4 wherein the undesirable vegetation is in a glyphosate tolerant crop.

* * * * *